(12) United States Patent
Kim et al.

(10) Patent No.: US 10,314,306 B2
(45) Date of Patent: Jun. 11, 2019

(54) BIO-CELLULOSE SHEET, BIO-CELLULOSE SHEET PRODUCT, AND PRODUCTION METHODS THEREOF

(71) Applicant: UROF, INC., Seoul (KR)

(72) Inventors: Seung Gyu Kim, Seoul (KR); Ki Seok Cheong, Seoul (KR)

(73) Assignee: UROF, INC., Seoul (KR)

( * ) Notice: Subject to any disclaimer, the term of this patent is extended or adjusted under 35 U.S.C. 154(b) by 7 days.

(21) Appl. No.: 15/615,367

(22) Filed: Jun. 6, 2017

(65) Prior Publication Data

US 2018/0092355 A1    Apr. 5, 2018

(30) Foreign Application Priority Data

Sep. 30, 2016   (KR) ................. 10-2016-0127013

(51) Int. Cl.

| | |
|---|---|
| *A01N 25/34* | (2006.01) |
| *A45D 34/04* | (2006.01) |
| *A61K 8/02* | (2006.01) |
| *A61K 8/81* | (2006.01) |
| *A61Q 19/10* | (2006.01) |
| *D04H 1/64* | (2012.01) |
| *A61K 36/889* | (2006.01) |
| *A61K 8/73* | (2006.01) |
| *A61K 8/9789* | (2017.01) |
| *A61K 8/9761* | (2017.01) |
| *A61K 8/9794* | (2017.01) |
| *A61K 8/9767* | (2017.01) |
| *A61K 8/9771* | (2017.01) |
| *A61K 36/76* | (2006.01) |
| *A61K 36/15* | (2006.01) |
| *A61K 36/16* | (2006.01) |
| *A61K 36/484* | (2006.01) |
| *A47K 10/32* | (2006.01) |
| *A61K 36/00* | (2006.01) |
| *A61Q 19/00* | (2006.01) |

(52) U.S. Cl.
CPC ............. *A01N 25/34* (2013.01); *A45D 34/04* (2013.01); *A61K 8/0208* (2013.01); *A61K 8/0212* (2013.01); *A61K 8/731* (2013.01); *A61K 8/81* (2013.01); *A61K 8/9761* (2017.08); *A61K 8/9767* (2017.08); *A61K 8/9771* (2017.08); *A61K 8/9789* (2017.08); *A61K 8/9794* (2017.08); *A61K 36/15* (2013.01); *A61K 36/16* (2013.01); *A61K 36/484* (2013.01); *A61K 36/76* (2013.01); *A61K 36/889* (2013.01); *A61Q 19/10* (2013.01); *D04H 1/64* (2013.01); *A45D 2200/1018* (2013.01); *A45D 2200/1027* (2013.01); *A45D 2200/1036* (2013.01); *A47K 2010/3266* (2013.01); *A61K 36/00* (2013.01); *A61K 2800/524* (2013.01); *A61K 2800/805* (2013.01); *A61Q 19/00* (2013.01)

(58) Field of Classification Search
CPC ....... A01N 25/34; A61K 8/0212; A61K 47/38
USPC ....................................................... 424/413
See application file for complete search history.

(56) References Cited

U.S. PATENT DOCUMENTS

| | | | |
|---|---|---|---|
| 8,668,923 B2 | 3/2014 | Saito et al. | |
| 2013/0244977 A1 | 9/2013 | Lee et al. | |
| 2013/0280310 A1* | 10/2013 | Suzuki ................. | A61Q 19/00 424/401 |
| 2013/0338078 A1 | 12/2013 | Galderisi | |

FOREIGN PATENT DOCUMENTS

| | | |
|---|---|---|
| CA | 2939895 A1 | 8/2015 |
| EP | 2808346 A1 | 12/2014 |
| FR | 2382891 A1 | 10/1978 |
| JP | 2009185417 A * | 8/2009 |
| KR | 10-2014-0076867 A | 6/2014 |
| KR | 10-2014-0129509 A | 11/2014 |
| KR | 10-2015-0090514 A | 8/2015 |
| KR | 10-1638371 B1 | 7/2016 |

OTHER PUBLICATIONS

Megan McIntyre, title: Sheet Masks: Creepy, Yet Wildly Effective Skin Care; Story from Skin Care, published Mar. 11, 2013. (Year: 2013).*

* cited by examiner

*Primary Examiner* — Yanzhi Zhang
(74) *Attorney, Agent, or Firm* — Korus Patent, LLC; Seong Il Jeong

(57) ABSTRACT

Disclosed herein are a bio-cellulose sheet without a supporting means, in which the bio-cellulose sheet includes coconut and contains a preservative including a plant extract, a bio-cellulose sheet product including the bio-cellulose sheet without a supporting means, and production methods thereof. The bio-cellulose sheet without a supporting means and the product including the same have a high content of a cosmetic composition, are less irritating to the skin, and are convenient to use. The use of the methods for producing the bio-cellulose sheet without a supporting means and the product including the bio-cellulose sheet results in increased efficiency and a reduced production cost.

11 Claims, 6 Drawing Sheets

A: 2.3mm     B: 1.2mm

A: 1.4mm     B: 0.9mm

BIO-CELLULOSE SHEET, BIO-CELLULOSE SHEET PRODUCT, AND PRODUCTION METHODS THEREOF

BACKGROUND

1. Technical Field

The present invention relates to a bio-cellulose sheet, a bio-cellulose sheet product, and production methods thereof.

2. Description of the Related Art

Sheets that are used in the cosmetic and medical fields are manufactured in specific shapes and attached to human bodies without requiring the need to take out and apply cream or emulsion-type cosmetics or ointments by hand. Such sheets are used for burn treatment, skin moisturizing, skin whitening or skin nutrition.

Mask sheets that are used in the cosmetic field generally assume the form of non-woven fabrics made of either vegetable cellulose fibers (derived from cotton or pulp) or synthetic fibers. Sheets made of such materials are suitable vehicles for cosmetic emulsions, and can be formed in various shapes depending on the body parts to which they are to be applied. Accordingly, such sheets are used for various purposes.

However, sheets made of cotton or non-woven fabrics are problematic in that they become dry within a short period of time after application to body parts and in that a foreign material, such as dust, together with the sheets, may also be attached to body parts. In order to overcome these problems, research into various other materials has been conducted in connection with a period of use, a wearing sensation, efficacy, etc.

As a result of this research, various types of sheets, including hydrogel-type sheets produced using natural agar or the like and bio-cellulose-type sheets produced through microbial culture, have been proposed in addition to non-woven fabric-type sheets. In particular, the bio-cellulose-type sheets produced through microbial culture cause fewer side effects on the human body because they are based on natural material. Furthermore, the bio-cellulose-type sheets have desirable physical strength because they are made of ultra-fine fibers. In addition, they are effective for skin moisturizing and skin nutrition because they have high moisture contents.

Bio-cellulose-type sheets, which are currently commercially available, generally include a supporting means configured to prevent bio-cellulose from slipping during cutting and mass production. The reason why the supporting means is used is that the bio-cellulose is inherently slippery. Accordingly, when such a bio-cellulose type sheet has no supporting means, the bio-cellulose type sheet cannot be formed in a desired shape. The supporting means may be of a non-woven fabric, mesh or film type. The supporting means is attached to one or both sides of the bio-cellulose sheet (see FIG. 1).

Where a supporting means is attached to a bio-cellulose mask sheet, a problem arises in that the bio-cellulose mask sheet itself cannot sufficiently contain a cosmetic composition because the cosmetic composition is absorbed into the supporting means attached to the mask sheet. Furthermore, inconvenience arises in that whenever a bio-cellulose sheet product having a supporting means attached thereto is used, it is required that a user removes the supporting means difficult to remove and then attaches the bio-cellulose sheet, from which the supporting means has been removed, to the body. Additionally, when the bio-cellulose sheet product is produced, a cumbersome additional process of attaching the supporting means to the bio-cellulose sheet is further required, and the cost of the supporting means itself is also added, thereby resulting in an increase in the cost of the product. Therefore, there is a need for the development of a bio-cellulose sheet which can be more easily used and which is relatively inexpensive.

Mask sheets that are used in the cosmetic field contain a preservative, and products comprising a bio-cellulose sheet also contain a preservative in order to prevent bacterial growth. Examples of preservatives that are used in cosmetics include methylparaben, ethylparaben, propylparaben, butylparaben, imidazolidinyl urea, and the like. Such synthetic parabens have been widely used in various types of cosmetics and perfumes. There are research results showing that such parabens may cause various diseases, including breast cancer, when they are accumulated in the human body. For this reason, there is a need for research into natural materials capable of replacing synthetic materials that have been currently used in cosmetics.

PRIOR ART DOCUMENTS

Patent Documents

Patent document 1: Korean Patent No. 10-1638371
Patent document 2: Korean Patent Application Publication No. 10-2014-0129509

SUMMARY

An object of the present invention is to provide a bio-cellulose sheet without a supporting means, in which the bio-cellulose sheet includes coconut and contains a preservative including a plant extract, and a product which includes the bio-cellulose sheet.

Another object of the present invention is to provide a method for producing a bio-cellulose sheet without a supporting means, the method including: preparing a cellulose material comprising coconut; immersing the cellulose material in a culture medium, and inoculating the immersed cellulose material with a strain, thereby producing bio-cellulose having a thickness of 150 to 200 mm; slicing the bio-cellulose to a thickness of 0.5 to 3.5 mm; whitening and washing the sliced bio-cellulose; sterilizing the whitened and washed bio-cellulose; soaking the sterilized bio-cellulose in a preservative including a plant extract; and dehydrating the preservative-soaked bio-cellulose, and pressing and cutting the dehydrated bio-cellulose without a supporting means; and is also to provide a bio-cellulose sheet without a supporting means and a bio-cellulose sheet product without a supporting means, which are produced by the above-described method.

However, objects that are achieved by the present invention are not limited to the above-described objects, and other objects that have not been described above will be apparently understood by those skilled in the art.

In accordance with one aspect of the present invention, there is provided a bio-cellulose sheet without a supporting means, in which the bio-cellulose sheet includes coconut and contains a preservative including a plant extract.

In accordance with one embodiment of the present invention, the plant extract includes an extract of any one of pine needles, licorice, *Thujopsis dolabrata*, Salix, *Elaeagnus umbellate*, *Berchemia berchemiaefolia*, and *Ginkgo biloba*.

In accordance with another aspect of the present invention, there is provided a bio-cellulose sheet product including the bio-cellulose sheet and a container.

In accordance with one embodiment of the present invention, the container of the bio-cellulose sheet product includes any one of glass, aluminum, porcelain, plastic resin, acryl, paper, vinyl, and polyethylene terephthalate/polypropylene (PET/PP).

In accordance with still another aspect of the present invention, there is provided a method for producing a bio-cellulose sheet without a supporting means, the method including: preparing a cellulose material including coconut; immersing the cellulose material in a culture medium, and inoculating the immersed cellulose material with a strain, thereby producing a bio-cellulose having a thickness of 150 to 200 mm; slicing the bio-cellulose to a thickness of 0.5 to 3.5 mm; whitening and washing the sliced bio-cellulose; sterilizing the whitened and washed bio-cellulose; soaking the sterilized bio-cellulose in a preservative including a plant extract; and dehydrating the preservative-soaked bio-cellouse, and pressing and cutting the dehydrated bio-cellulose without a supporting means.

In accordance with one embodiment of the present invention, sterilizing the whitened and washed bio-cellulose is performed at a temperature of 100 to 200° C. for 15-30 minutes.

In accordance with one embodiment of the present invention, the plant extract used in soaking the sterilized bio-cellulose includes an extract of any one of pine needles, licorice, *Thujopsis dolabrata*, Salix, *Elaeagnus umbellate*, *Berchemia berchemiaefolia*, and *Ginkgo biloba*.

In accordance with one embodiment of the present invention, pressing and cutting the dehydrated bio-cellulose are simultaneously performed.

In accordance with one embodiment of the present invention, pressing and cutting the dehydrated bio-cellulose are performed using a press cutter including an upper half having air holes and a lower half having a portion configured to support the bio-cellulose.

In accordance with one embodiment of the present invention, the upper half having the air holes includes a slip-preventing portion.

In accordance with one embodiment of the present invention, the slip-preventing portion includes any one of sugar cane, plastic resin, and silicone resin.

In still another aspect of the present invention, there is provided a bio-cellulose sheet without a supporting means, which is produced by the method for producing the bio-cellulose sheet.

In still another aspect of the present invention, there is provided a method for producing a bio-cellulose sheet product without a supporting means, the method including: placing the bio-cellulose sheet, produced by the method for producing the bio-cellulose sheet, in a container; and sealing the container, and treating the sealed container with gamma rays.

In accordance with one embodiment of the present invention, the container includes any one of glass, aluminum, porcelain, plastic resin, acryl, paper, vinyl, and polyethylene terephthalate/polypropylene (PET/PP).

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
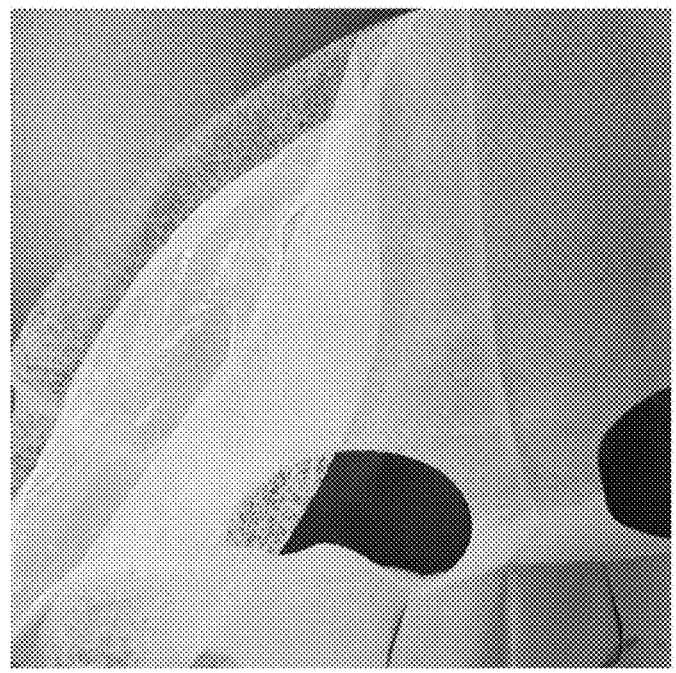
FIG. 1 shows the shape of a conventional bio-cellulose sheet.

Embodiments of the present invention will be described in detail below with reference to the accompanying drawings. Throughout the drawings, the same reference symbols designate the same components.

The following embodiments may be modified in various forms. It should be understood that the present invention is not limited to the following specific embodiments but rather encompasses all modifications, equivalents and alternatives falling within the scope of the present invention defined by the appended claims.

The terms used herein are intended only to illustrate specific embodiments, but are not intended to limit the present invention. Singular expressions include plural expressions unless specified otherwise in the context thereof. In the specification and the claims, the terms "include", "comprise", "have", etc. are intended to designate the presence of described characteristics, numbers, steps, operations, components, parts, or combinations thereof, but do not exclude the probability of the presence or addition of one or more other characteristics, numbers, steps, operations, components, parts, or combinations thereof.

Unless otherwise defined, all terms used herein, including technical or scientific terms, have the same meanings as understood by those having ordinary knowledge in the technical field to which the present invention pertains. The terms used commonly and defined in dictionaries should be interpreted as having meanings identical to those specified in the context of related technologies. Unless definitely defined herein, these terms should not be interpreted as having excessively formative meanings.

In the following description to be given with reference to the accompanying drawings below, the same components are designated by the same reference symbols, and redundant descriptions of these components will be omitted. In the following description of the embodiments, detailed descriptions of related known technologies will be omitted when they may unnecessarily make the gist of the present invention obscure.

The term "cellulose" used herein refers to cellulose that is the main component of the cell wall of plants and that constitutes plant fiber. The cellulose used herein is derived chiefly from cotton. The term "bio-cellulose" used herein refers to cellulose produced through microbial culture. More specifically, the term "bio-cellulose" refers to cellulose that is produced by inoculating a cellulose material with various strains and immersing the inoculated cellulose material in a culture medium. The term "bio-cellulose sheet" used herein refers to a sheet that is produced by slicing bio-cellulose to a suitable thickness and forming the sliced bio-cellulose into a shape that can be attached to the body. The term "bio-cellulose sheet" used herein is intended to encompass both a bio-cellulose sheet with a supporting means and a bio-cellulose sheet without a supporting means. When required, the two types of sheets are described as being distinct from each other. The term "supporting means" used herein refers to a non-woven fabric-, film- or mesh-type material that is attached to one or both sides of the bio-cellulose sheet in order to facilitate the cutting and support of bio-cellulose. The term "bio-cellulose sheet product" refers to a product that is produced by producing a bio-cellulose sheet having a shape attachable to the human body and introducing the produced bio-cellulose sheet into a container.

First, it should be noted that the embodiment of the present invention is advantageous in that the convenience of use of the bio-cellulose product and the effect of the bio-cellulose product can be improved by eliminating a supporting means which has caused problems for conventional bio-cellulose products and in that the production cost and the number of steps of a production process can be significantly reduced by eliminating the supporting means which has been used in the production process due to the slippery and sticky properties of bio-cellulose.

Although it is true that bio-cellulose is an excellent material for a mask pack, conventional mask pack sheets that inevitably comprise a supporting means due to the production process thereof have a problem in that the active ingredient of a cosmetic essence is absorbed into the supporting means. Various nonwoven fabric materials that are used as the supporting means interfere with the absorption of a cosmetic essence into mask pack sheets, and act like filtering meshes that filter out the active ingredient of the cosmetic essence. Accordingly, in this case, the active ingredient of the cosmetic essence is not appropriately soaked into the mask pack sheets. Nonetheless, the supporting means has been inevitably used due to the slippery and sticky properties of bio-cellulose.

Therefore, the elimination of a supporting means, such as a cover sheet, from a bio-cellulose mask sheet not only corresponds to the elimination of an unnecessary part from a conventional product, but also corresponds to an innovative invention based on a conversion of thinking, which employs a new technology and eliminates a process that has been inconvenient and unnecessary but must have been inevitably carried out.

The advantages of the present invention are as follows:

First, contamination and bacterial growth, which may occur in the process of attaching a supporting means, can be prevented. A bio-cellulose sheet having a supporting means and the same bio-cellulose sheet having no supporting means were tested for bacteria. As a result, the bacterial concentration of the bio-cellulose sheet having a supporting means was $1.6 \times 10^8$ CFU/g, whereas the bacterial concentration of the bio-cellulose sheet having no supporting means was reduced to less than $10^4$ CFU/g.

Figure 6A:
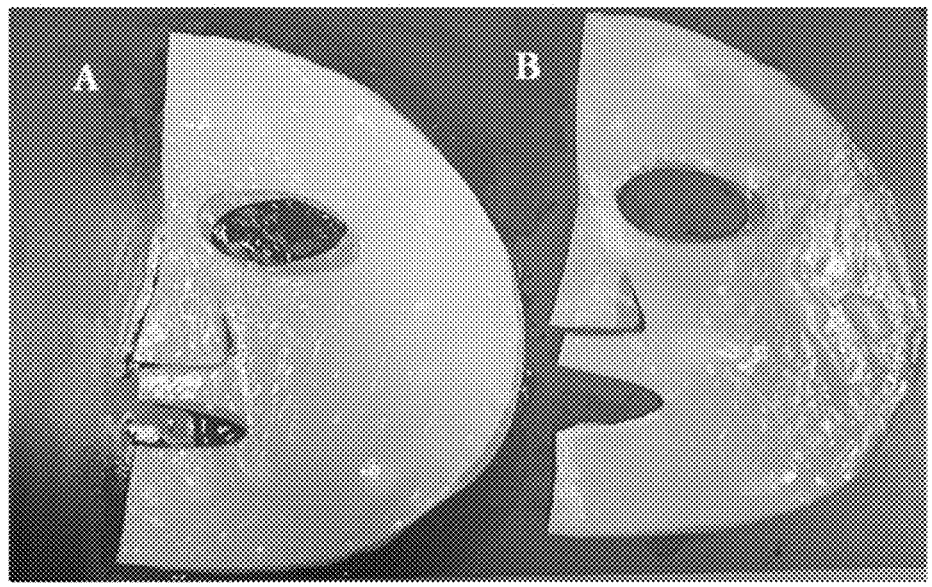
FIG. 6a shows a photograph of a bio-cellulose sheet immediately after soaking with a cosmetic essence.
Figure 6B:
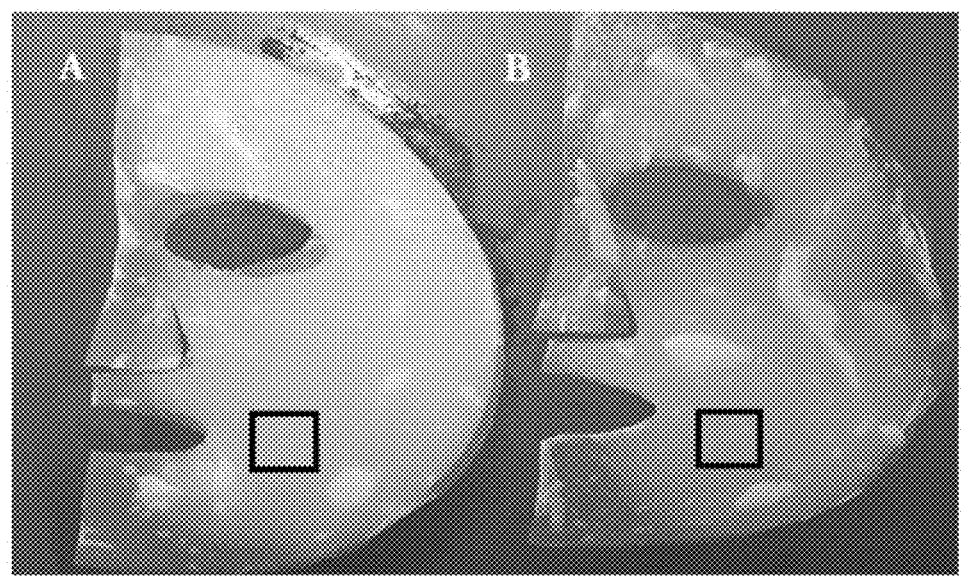
FIG. 6b shows a photograph of the bio-cellulose sheet after 24 hours.

Second, when the supporting means is eliminated, the absorption of a cosmetic essence into bio-cellulose increases, and the moisture retention capability of the bio-cellulose sheet increases. Where the thickness of a bio-cellulose sheet before soaking with a cosmetic essence was 0.7 mm, the thickness of a bio-cellulose sheet A having no supporting means was 2.3 mm after soaking, whereas the thickness of a bio-cellulose sheet B having a supporting means was 1.2 mm after soaking. After 24 hours, the thickness of the bio-cellulose sheet A having no supporting means was 1.4 mm, whereas the thickness of the bio-cellulose sheet B having a supporting means was reduced to 0.9 mm. FIG. 6a shows a photograph of a bio-cellulose sheet immediately after soaking with a cosmetic essence, and FIG. 6b shows a photograph of the bio-cellulose sheet after 24 hours.

Third, when the supporting means is eliminated, the active ingredient of a cosmetic essence can be effectively absorbed into bio-cellulose and delivered into the skin.

Figure 7A:
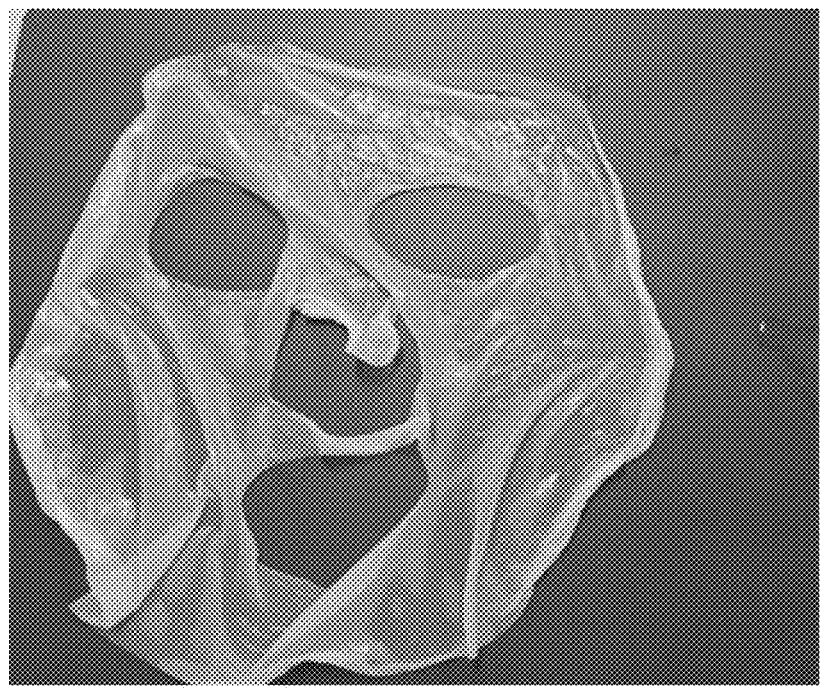
FIG. 7a is a photograph of a bio-cellulose sheet having a supporting means, taken after 1 hour of soaking with a cosmetic essence.
Figure 7B:
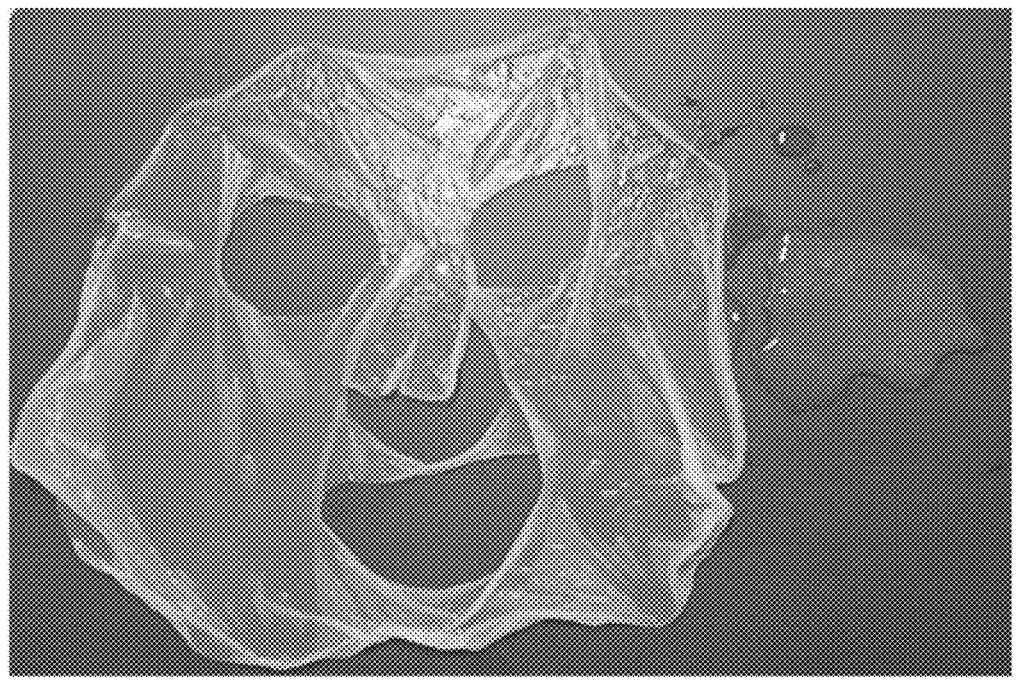
FIG. 7b is a photograph of a bio-cellulose sheet having no supporting means, taken after 1 hour of soaking with a cosmetic essence.

FIG. 7a is a photograph of a bio-cellulose sheet having a supporting means, taken after 1 hour of soaking with a cosmetic essence, and FIG. 7b is a photograph of a bio-cellulose sheet having no supporting means, taken after 1 hour of soaking with a cosmetic essence. In the case of the bio-cellulose sheet having a supporting means, the concentration of the cosmetic essence was low, the remaining amount of the cosmetic essence was also small, and the viscosity was 20 mPaS. In contrast, in the case of the bio-cellulose sheet having no supporting means, the concentration of the cosmetic essence was high, the remaining amount of the cosmetic essence was large, and the viscosity was 45 PaS. When the supporting means is present, it filters out the active ingredient of a cosmetic essence, and thus the effect of the cosmetic essence is rarely achieved. In contrast, when the supporting means is absent, an increased amount of a cosmetic essence can be effectively absorbed into the skin.

Fourth, the time taken to remove a cover sheet (i.e., the supporting means) from a mask sheet in order to use the mask sheet can be eliminated.

The present inventor measured the times taken for 14 persons to remove supporting means from cellulose sheets. The averages of the measured times were 1 minute and 32 seconds for Asians and about 2 minutes for Westerners. This suggests that the attachment of the supporting means has a significant adverse effect on the convenience of use of products.

Fifth, when the supporting means is eliminated, the production cost and the product cost can be reduced.

In accordance with one aspect of the present invention, there is provided a bio-cellulose sheet without a supporting means, in which the bio-cellulose sheet includes coconut and contains a preservative including a plant extract.

The bio-cellulose sheet is a sheet including coconut as a main component, and is produced by immersing a cellulose material in a medium for microbial culture and inoculating the immersed cellulose material with a strain. Coconut is advantageous in that it abundantly contains cellulose necessary for the production of bio-cellulose and can be easily processed. Meanwhile, the bio-cellulose sheet including coconut may contain a sufficient quantity of cosmetic composition or moisture because a cellulose component is very densely formed therein. In addition, the bio-cellulose sheet is less irritating to the skin because it is composed of a natural material. Coconut that is used in the present invention may be either in the form of coconut flesh cut into a suitable shape or in the form of crushed coconut flesh.

A preservative is added to the bio-cellulose sheet in order to prevent bacterial growth, etc. In the prior art, paraben-based preservatives have been used in cosmetics in order to inhibit bacteria or fungi. However, in recent years, the use of such parabens has been refrained from due to the results of studies indicating that such parabens are harmful to the human body. Bio-cellulose provides an environment advantageous for bacterial growth, and for this reason, a preservative should necessarily be added thereto. Accordingly, according to the present invention, a preservative including a plant extract that is harmless to the human body is used as a substitute for synthetic materials that have been used in the prior art, thereby enabling the bio-cellulose sheet to be used without worries. The preservative may further include another component that is commonly used.

Figure 2:
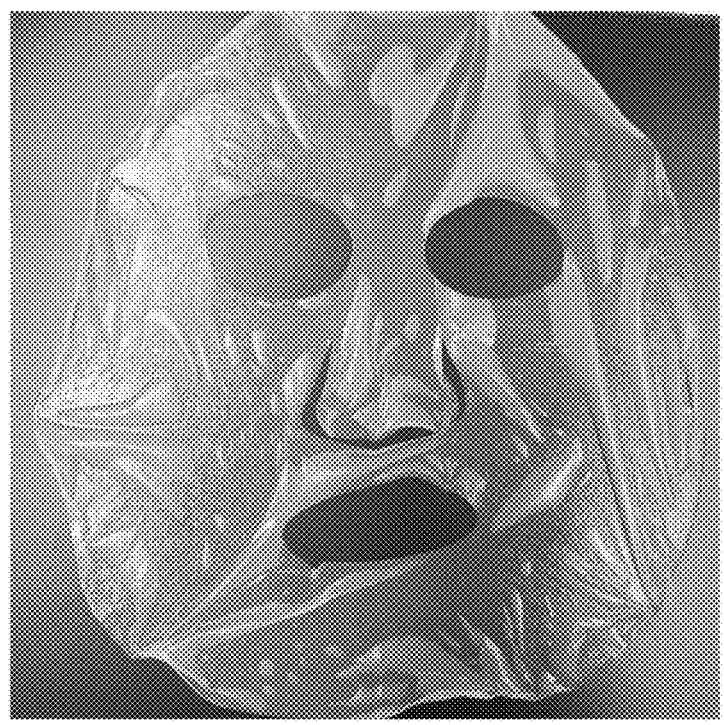
FIG. 2 shows a bio-cellulose sheet according to an example of the present invention.

The bio-cellulose sheet includes coconut as a main component, and thus provides slippery and soft sensations. Due to these properties of bio-cellulose material, bio-cellulose sheets are difficult to fasten in a predetermined position. For this reason, conventional bio-cellulose sheets necessitate a supporting means. In other words, bio-cellulose sheets having a supporting means have been used. The reason for this is that a bio-cellulose sheet can be fastened in a predetermined position only when the bio-cellulose sheet has a supporting means and the bio-cellulose sheet can be cut into a desired shape (a specific shape, a specific size, etc.) only when it is fastened in the predetermined position (see FIG. 1). Generally, a supporting means that is used to prevent bio-cellulose from slipping during the cutting thereof is composed of a non-woven fabric, mesh or film made of cotton or synthetic fiber, and is used in the state of being attached to one or both sides of a bio-cellulose sheet. However, the present invention provides a bio-cellulose sheet without a supporting means (see FIG. 2). Where a bio-cellulose sheet without a supporting means is used, it is convenient in that a supporting means does not need to be removed from one or both sides of the sheet. Furthermore, since a cosmetic composition is prevented from being unnecessarily absorbed into a supporting means, the content of a cosmetic composition in the bio-cellulose sheet itself is significantly higher than that in a bio-cellulose sheet with a supporting means. Moreover, where the bio-cellulose sheet without a supporting means is used, the price of a sheet product including the bio-cellulose sheet without a supporting means can be also significantly reduced.

In accordance with one embodiment of the present invention, the plant extract used in the bio-cellulose sheet without a supporting means includes an extract of any one of pine needles, licorice, *Thujopsis dolabrata*, Salix, *Elaeagnus umbellate*, *Berchemia berchemiaefolia*, and *Ginkgo biloba*.

Examples of plants, from which an extract that may be contained in the preservative is obtained, include pine needles, licorice, *Thujopsis dolabrata*, Salix, *Elaeagnus umbellate*, *Berchemia berchemiaefolia*, *Ginkgo biloba*, and the like. Since an extract of pine needles, licorice, *Thujopsis dolabrata*, Salix, *Elaeagnus umbellate*, *Berchemia berchemiaefolia*, or *Ginkgo biloba* has antibacterial effects, it can substitute for synthetic preservatives that are harmful to the human body. In particular, the pine needle extract is preferable because it contains a large amount of phytoncide having an antioxidant effect. This plant extract that is contained in the preservative can be obtained by performing extraction from a plant by means of a commonly used percolation extraction process and isolating and purifying the extract. The preservative is preferably contained in an amount of 0.1-5 wt %, more preferably 1-3 wt %, based on 100 wt % of the bio-cellulose sheet.

In accordance with one aspect of the present invention, there is provided a bio-cellulose sheet product, including a bio-cellulose sheet without a supporting means and a container. The term "bio-cellulose sheet product" used herein refers to a product obtained by placing a bio-cellulose sheet, produced from a bio-cellulose material including coconut, in a container, and also refers to a product into which a cosmetic composition has not yet been introduced. The present invention may provide bio-cellulose products obtained by placing the above-described bio-cellulose sheet in containers in various forms. Since the bio-cellulose sheet without a supporting means is not rigid, it may be crumpled into a shape like crumpled toilet paper and placed in a container. In addition, the bio-cellulose sheet without a supporting means may also be placed in a container after being folded to ½ or ¼ (see FIG. 3). Alternatively, the present invention may also provide a product obtained by rolling up the bio-cellulose sheet and placing the rolled sheet in a tube-type container. Since the bio-cellulose sheet can be deformed into various shapes depending on the shape of a container, bio-cellulose products having various shapes may be provided. The container containing the bio-cellulose sheet may be made of any one of glass, aluminum, porcelain, plastic resin, acryl, paper, vinyl, and polyethylene terephthalate/polypropylene (PET/PP). A glass container allowing the sheet to be visible may be used, and a porcelain container having an aesthetic effect may also be used. In addition, a flexible plastic container may also be used, and a container made of acrylic resin may also be used. Regardless of the type of material forming the container, the container may have various shapes.

In accordance with another aspect of the present invention, there is provided a method for producing a bio-cellulose sheet without a supporting means, the method including the steps of: preparing a cellulose material including coconut; immersing the cellulose material in a culture medium, and inoculating the immersed cellulose material with a strain, thereby producing a bio-cellulose having a thickness of 150 mm to 200 mm; slicing the bio-cellulose to a thickness of 0.5 mm to 3.5 mm; whitening and washing the sliced bio-cellulose; sterilizing the whitened and washed bio-cellulose; soaking the sterilized bio-cellulose in a preservative including a plant extract; and dehydrating the preservative-soaked bio-cellulose, and pressing and cutting the dehydrated bio-cellulose.

The coconut that is used in the step of preparing the bio-cellulose material including coconut may be unprocessed coconut flesh or crushed coconut flesh. In addition, various other methods may be used as long as they can compress and form coconut into a sheet shape.

The unprocessed coconut flesh or crushed coconut flesh is immersed in a culture medium, after which it is inoculated with a strain and subjected to stationary culture, thereby producing a bio-cellulose material having a thickness of 150 to 200 mm. The strain that is used in the present invention may be *Acetobacter xylinum*. In addition, the strain may be a microbial strain, such as *Gluconacetobacter* sp., *Agrobacterium* sp., *Rhizobium* sp., *Pseudomanas* sp., *Sarcina* sp., or the like. The microbial strain is cultured at a temperature of 20 to 40° C. for 5-10 days, which are conditions optimal for the growth of the microorganisms that produce bio-cellulose.

The produced bio-cellulose is sliced to a thickness of 0.5-3.5 mm, preferably 1.5-2.7 mm. In this thickness range, when a cosmetic composition is introduced therein and used for a mask sheet, the sliced bio-cellulose can be easily attached to the body, and can also have a high moisture content.

The sliced bio-cellulose is whitened using a conventional method and washed three times or more with purified water. The washed bio-cellulose is dehydrated in a centrifuge for about 10 minutes to sufficiently remove water, so that it can sufficiently absorb a preservative. The washed bio-cellulose is sterilized at a temperature of 100 to 120° C. for 15-30 minutes. Thereafter, the sterilized bio-cellulose is soaked in a preservative including a plant extract for 10 minutes to 24 hours.

The plant extract that is included in the preservative may be an extract of pine needles, licorice, *Thujopsis dolabrata*, Salix, *Elaeagnus umbellate, Berchemia berchemiaefolia*, or *Ginkgo biloba*. In particular, the pine needle extract is more preferable because it contains a large amount of phytoncide having an antioxidant effect. This plant extract that is contained in the preservative can be obtained by performing extraction from a plant by means of a conventional percolation extraction process and isolating and purifying the extract. The preservative is preferably contained in an amount of 0.1-5 wt %, more preferably 1-3 wt %, based on 100 wt % of the bio-cellulose sheet.

Figure 4:
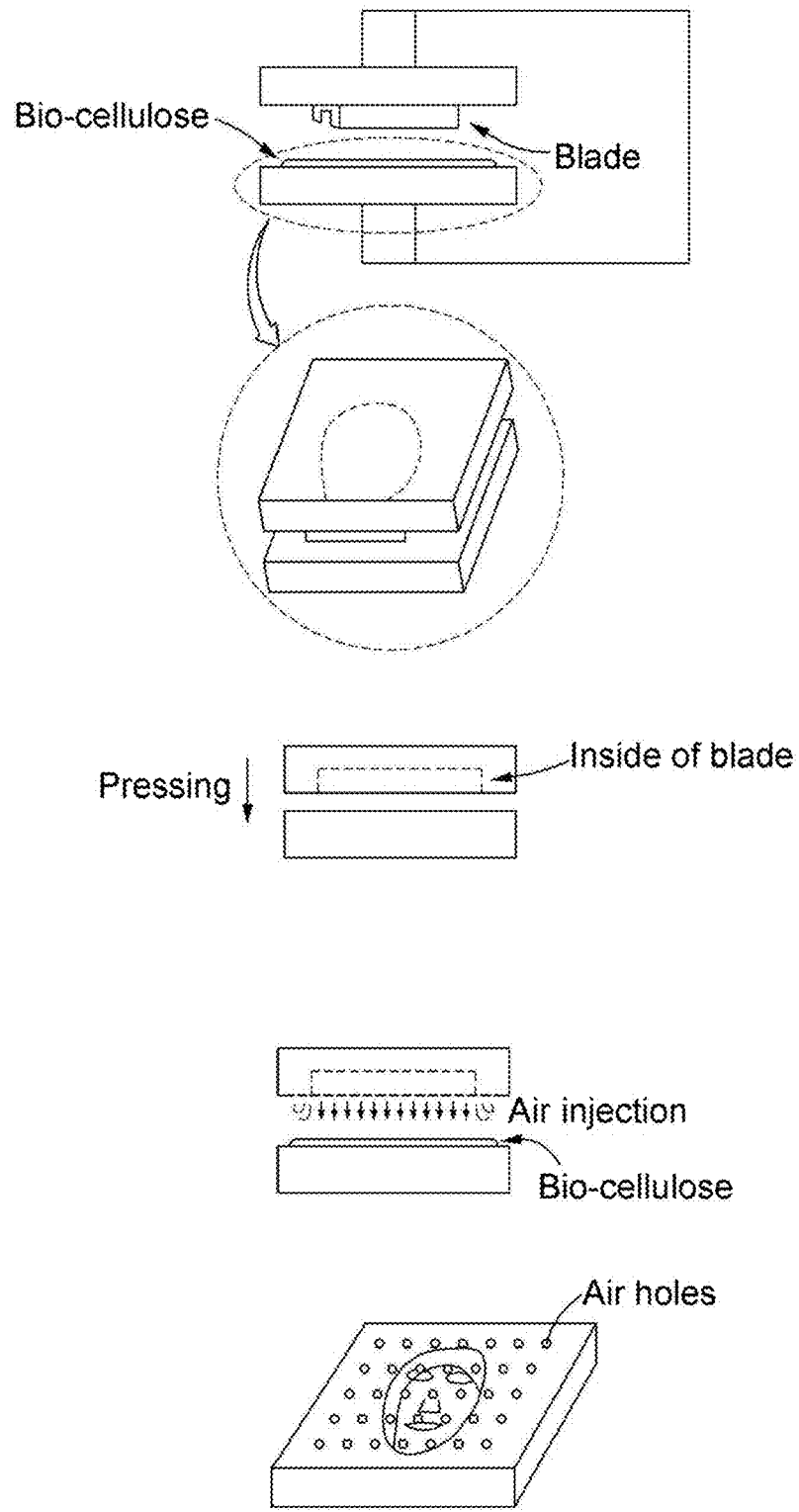
FIG. 4 shows a part of a method for producing a bio-cellulose sheet according to an example of the present invention.
Figure 5:
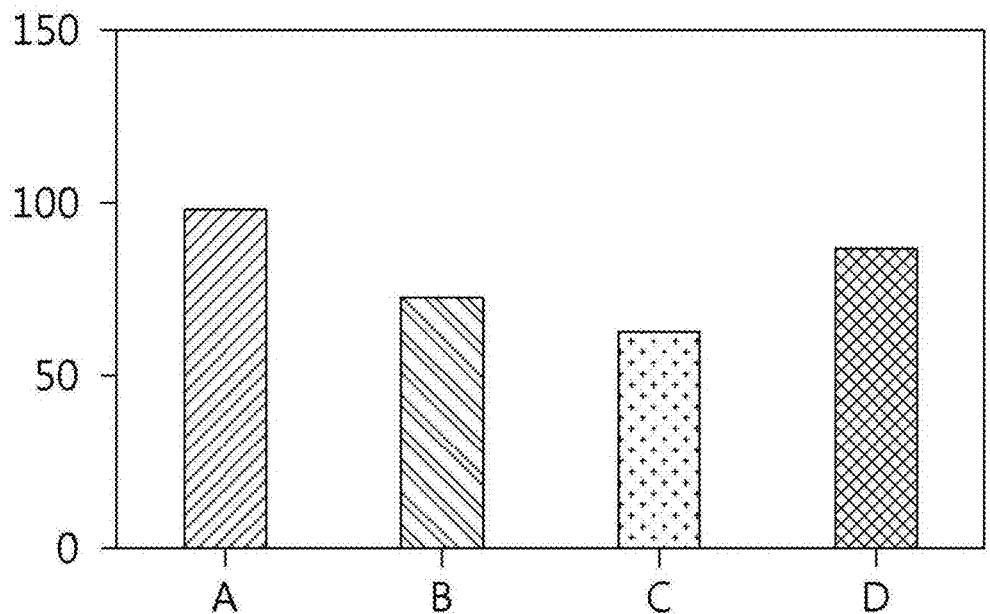
FIG. 5 is a graph showing the comparisons of moisture contents between a bio-cellulose sheet without a supporting means according to the present invention and bio-cellulose sheets with a supporting means.

After the bio-cellulose has been soaked in the preservative, the bio-cellulose is pressed and cut. A press cutter that is used for the pressing and cutting of the bio-cellulose may be a hand- or power-operated press cutter, and may also be of a lever or press type. Where the press cutter is used, the bio-cellulose can be pressed to remove the remaining water, and can also be cut to a desired shape. The upper half of the press cutter has a blade attached to the inner surface thereof. When the bio-cellulose is pressed, the blade cuts the bio-cellulose, and can also be inserted into the upper half. The blade of the press cutter can be appropriately selected depending on the intended use of the product, and can cut the bio-cellulose to various shapes. In particular, when a mask sheet to be used for cosmetic applications is to be produced, a press cutter including a face-shaped blade in the upper half thereof may be used for cutting. The press cutter includes an upper half having air holes and a lower half having a portion configured to support the bio-cellulose. Preferably, a plurality of air holes is formed in the upper half. During the pressing and cutting process, air can be injected from the air holes and can prevent the bio-cellulose from being attached to the upper half of the press cutter. Accordingly, after the bio-cellulose has been cut to a desired shape, the bio-cellulose sheet can be easily removed from the press cutter. Meanwhile, the upper half having the air holes may include a slip-preventing portion. To cut a slippery material such as coconut, the shape of the material needs to be fastened. For this reason, in a conventional prior art, a method for attaching a supporting means to one or both sides of a bio-cellulose sheet before the cutting of the sheet has been used. In other words, in a conventional art, a supporting means made of a non-woven fabric, a mesh, or a film is attached to one or both sides of bio-cellulose, and prevents the bio-cellulose from slipping during pressing and cutting. Where the press cutter including the slip-preventing portion is used, the bio-cellulose can be fastened in a predetermined position even when the bio-cellulose includes no supporting means. In addition, in this case, the bio-cellulose can also be easily cut. Although the slip-preventing portion may include any one of sugar cane, plastic resin and silicone resin, it is not limited thereto as long as it is made of a material that enables a slippery material to be fastened in a predetermined position (see FIG. 4).

In still another aspect, the present invention provides a bio-cellulose sheet without a supporting means, which is produced by the above-described method. According to the above-described method, it is possible to produce a bio-cellulose sheet which has no supporting means and which contains a preservative including a plant extract.

Figure 3:
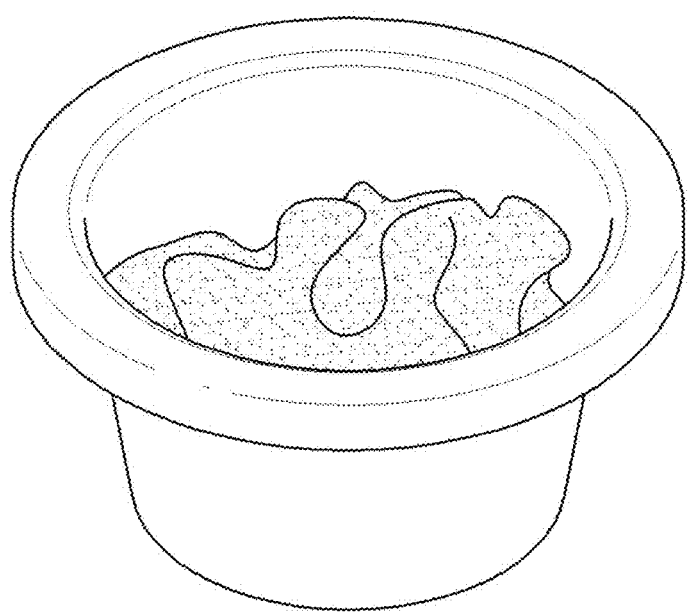
FIG. 3 shows a bio-cellulose sheet product obtained by placing a bio-cellulose sheet in a container according to an example of the present invention.

According to one embodiment of the present invention, a bio-cellulose sheet product without a supporting means may be produced by a method including the steps of: placing the above-described bio-cellulose sheet in a container; and sealing the container and treating the sealed container with gamma-rays. The container may be made of any one of glass, aluminum, porcelain, plastic resin, acryl, paper, vinyl, and polyethylene terephthalate/polypropylene (PET/PP). Generally, when a bio-cellulose sheet with a supporting means is to be introduced, the bio-cellulose sheet is placed in a pouch-type container after being folded to ¼ of its original size. However, a bio-cellulose sheet without a supporting means may be freely deformed so as to be suitable for the shape of a container. In other words, where a container as shown in FIG. 3 is used, the bio-cellulose sheet may be crumpled and placed in a container. Preferably, the bio-cellulose sheet may be rolled up, and the rolled sheet may be placed and stored in a tube-type container. After the bio-cellulose sheet has been placed in the container, the gap between the cap and the container is sealed, and the container is sterilized with gamma-rays. When a cosmetic composition having special effects, such as skin whitening, wrinkle prevention, nutrition or the like, is impregnated into the bio-cellulose sheet product produced as described above, a cosmetic mask pack sheet suitable for commercial applications is obtained. The type of cosmetic composition that is impregnated into the bio-cellulose sheet product is not limited and may be appropriately selected depending on the intended use. When the cosmetic composition is impregnated into the bio-cellulose sheet product, the bio-cellulose sheet will absorb the cosmetic composition. Due to the property of the bio-cellulose material, when the seal of the product having the cosmetic composition impregnated therein is opened and the bio-cellulose sheet is taken out from the product, the sheet will be easily unfolded into a shape that can be attached to the human body. For this reason, the bio-cellulose sheet may be deformed into various shapes and placed in a variety of containers. Where a bio-cellulose sheet including an anti-slip slip is used, the frequency at which the sheet comes into contact with an external environment in the process of folding the sheet increases. For this reason, bacteria will more easily grow in the sheet. However, where the bio-cellulose sheet without a supporting means is used, the process of folding the sheet can be omitted, and thus bacterial growth within the sheet can be reduced.

The present invention will be described in detail below with reference to examples. It is to be understood, however, that these examples are presented for illustrative purposes only and are not intended to limit the scope of the present invention.

Example 1: Step of Preparing Bio-Cellulose

Undiluted coconut milk obtained by crushing coconut was placed on a tray (24 cm×34 cm (W×L)), and 1 wt % of sugar was added thereto. Thereafter, the coconut milk was inoculated with *Acetobacter xylinum* and incubated at room temperature for about 8-10 days, thereby producing bio-cellulose. The produced bio-cellulose was sliced, whitened, washed, and then sterilized at a temperature of 100 to 150° C. for 15 minutes.

Example 2: Method for Preparing Preservative Including Plant Extract

In order to prepare a plant extract to be contained in a preservative, Salix twigs were cut finely to a size of 2-3 cm, and then dried. The crushed and dried Salix twigs were placed in an extractor which was then sealed. The sealed extractor was heated to a temperature of 50 to 60° C. by operating a heater, and then an extract is obtained from the plant through percolation. The extract was isolated and purified through centrifugation, and concentrated in a rotary evaporator at increased temperature under reduced pressure. Glycerin was added to the concentrated extract to thereby prepare a preservative. The bio-cellulose prepared as described above was soaked in the preservative containing the Salix extract.

Example 3: Step of Pressing and Cutting Bio-Cellulose Sheet without Supporting Means In order to dehydrate the prepared bio-cellulose to a suitable moisture content and produce a sheet having a desired shape and size, the bio-cellulose was pressed and cut. In order to produce a bio-cellulose sheet to be used on the face, a press cutter including a face-shaped blade was used, and pressing and cutting of the bio-cellulose were simultaneously performed by using a hand-operated lever. During the pressing and cutting, air were injected from air holes in the upper half of the press cutter. The cut bio-cellulose sheet was removed from the press cutter.

Example 4: Step of Producing Bio-Cellulose Sheet Product

The produced bio-cellulose sheet was placed in a plastic container without being folded into a specific shape. The plastic container was sealed, and then sterilized with gamma-rays in such a manner that the bio-cellulose sheet would not be contaminated or external air would not flow into the container, thereby producing a bio-cellulose sheet product.

Example 5: Test for Comparison of Moisture Contents Between Bio-Cellulose Sheet with Supporting Means and Bio-Cellulose Sheet without Supporting Means A cosmetic composition was impregnated into each of a bio-cellulose sheet A without a supporting means, produced in Example 3, and three types of commercially available bio-cellulose sheets B, C and D with a supporting means, and the contents of moisture were compared between the sheets.

More specifically, the prepared bio-cellulose was sufficiently dehydrated by means of a centrifuge for 10 minutes or more so that a cosmetic composition could be easily absorbed into the prepared bio-cellulose. Using the dehydrated bio-cellulose, the following four types of bio-cellulose sheets were produced, and each of the four types of sheets was placed in a pouch which was then sealed. 30 g of the same cosmetic composition was introduced into the sealed pouches which were then stored at room temperature for 24 hours, after which the contents of moisture in the sheets were tested. The supporting means were removed from the bio-cellulose sheets B, C and D which were then compared with the bio-cellulose sheet A without a supporting means.

As a result, the bio-cellulose sheet A exhibited a moisture content of about 98% (containing about 29 g of the cosmetic composition; the bio-cellulose sheet B exhibited a moisture content of about 73% (containing about 22 g of the cosmetic composition); the bio-cellulose sheet C exhibited a moisture content of about 63% (containing about 19 g of the cosmetic composition); and the bio-cellulose sheet exhibited a moisture content of about 87% (containing about 26 g of the cosmetic composition). In other words, in the cases of the bio-cellulose sheets with a supporting means, the amount of cosmetic composition absorbed into the supporting means was large, and thus the amount of cosmetic composition absorbed into the bio-cellulose sheet was reduced.

The four types of bio-cellulose sheets are as follows:

A: the bio-cellulose sheet not including a supporting means

B the bio-cellulose sheet including a non-woven fabric, attached to both sides of bio-cellulose, as a supporting means C: the bio-cellulose sheet including a non-woven fabric, attached to one side of bio-cellulose, and a film, attached to the other side, as a supporting means D: the bio-cellulose sheet including a mesh material, attached to both sides of bio-cellulose, as a supporting means As described above, the present invention provides a bio-cellulose sheet without a supporting means, in which the bio-cellulose sheet includes coconut and contains a preservative including a plant extract. A user who uses the present invention can easily use the sheet without the inconvenience of removing a supporting means, and a manufacturer who produces the sheet of the present invention can omit the process of attaching a supporting means, thereby reducing the cost required for the attachment of a supporting means.

Meanwhile, the bio-cellulose sheet without a supporting means according to the present invention has a high content of a cosmetic composition compared to conventional bio-cellulose sheets, and thus can provide sufficient skin moisturizing and nutrition. In addition, according to the present invention, the process of attaching a supporting means configured to prevent bio-cellulose from slipping during the pressing and cutting of the bio-cellulose is not required, and thus bacterial growth that may occur between the supporting means and the bio-cellulose sheet can be eliminated. Furthermore, the bio-cellulose sheet according the present invention includes a natural preservative based on a vegetable material, and thus is harmless to the human body.

While the present invention has been illustrated and described with reference to the limited examples and drawings, it will be apparent to those skilled in the art that various modifications and variations can be made based on the foregoing description. For example, appropriate effects can be achieved even when the foregoing processes and methods are carried out in an order different from the above-described order and/or the described components are combined or coupled in a form different from the above-described form or are replaced with other components or equivalents.

Therefore, other implementations, other embodiments, and equivalents to the appended claims should be construed as falling within the appended claims.

What is claimed is:

1. A method for producing a bio-cellulose sheet without a support, the method comprising:

preparing a cellulose material comprising coconut flesh;
immersing the cellulose material in a culture medium, and inoculating the immersed cellulose material with a microbial strain selected from the group consisting of *Acetobacter xylinum, Gluconacetobacter* sp., *Agrobacterium* sp., *Rhizobium* sp., *Pseudomanas* sp., and *Sarcina* sp., thereby producing bio-cellulose;
slicing the bio-cellulose to a predetermined thickness;
sterilizing the bio-cellulose;

soaking the sterilized bio-cellulose in a preservative comprising a plant extract; and dehydrating the preservative-soaked bio-cellulose, and pressing and cutting the dehydrated bio-cellulose without a support.

2. The method of claim 1, wherein whitening and washing the sliced bio-cellulose is performed before the sterilizing the bio-cellulose.

3. The method of claim 2, wherein the predetermined thickness ranges from 0.5 to 3.5 mm.

4. The method of claim 3, wherein sterilizing the whitened and washed bio-cellulose is performed at a temperature of 100 to 200° C. for 15-30 minutes.

5. The method of claim 3, wherein the plant extract used in soaking the sterilized bio-cellulose comprises an extract of any one of pine needles, licorice, *Thujopsis dolabrata, Salix, Elaeagnus umbellate, Berchemia berchemiaefolia*, and *Ginkgo biloba*.

6. The method of claim 3, wherein pressing and cutting the dehydrated bio-cellulose are simultaneously performed.

7. The method of claim 3, wherein pressing and cutting the dehydrated bio-cellulose are performed using a press cutter comprising an upper half having air holes and a lower half having a portion configured to place the bio-cellulose thereon.

8. The method of claim 7, wherein the upper half having the air holes comprises a slip-preventing portion.

9. The method of claim 8, wherein the slip-preventing portion comprises any one of sugar cane, plastic resin, and silicone resin.

10. The method of claim 1, wherein the method further comprising placing the bio-cellulose sheet without a support produced according to the method of claim 1 in a container; sealing the container, and treating the sealed container with gamma rays.

11. The method of claim 10, wherein the container comprises any one of glass, aluminum, porcelain, plastic resin, acryl, paper, vinyl, and polyethylene terephthalate/polypropylene (PET/PP).

* * * * *